(12) United States Patent
Yamada et al.

(10) Patent No.: US 10,828,435 B2
(45) Date of Patent: Nov. 10, 2020

(54) NON-COMBUSTION TYPE FLAVOR INHALER, FLAVOR SOURCE UNIT, AND METHOD FOR MANUFACTURING MEMBER USED IN A NON-COMBUSTION TYPE FLAVOR INHALER

(71) Applicant: JAPAN TOBACCO INC., Tokyo (JP)

(72) Inventors: Manabu Yamada, Tokyo (JP); Akihiko Suzuki, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 510 days.

(21) Appl. No.: 15/657,504

(22) Filed: Jul. 24, 2017

(65) Prior Publication Data

US 2017/0319799 A1 Nov. 9, 2017

Related U.S. Application Data

(63) Continuation of application No. PCT/JP2015/066258, filed on Jun. 4, 2015.

(30) Foreign Application Priority Data

Jan. 26, 2015 (WO) .................. PCT/JP2015/052063

(51) Int. Cl.
*A61M 15/06* (2006.01)
*A24F 47/00* (2020.01)
(Continued)

(52) U.S. Cl.
CPC ............. *A61M 15/06* (2013.01); *A24F 47/00* (2013.01); *A24F 47/008* (2013.01);
(Continued)

(58) Field of Classification Search
CPC .. A24F 7/008; A24F 7/002; A24F 7/00; A24F 7/004; A24F 40/00; A24F 40/10;
(Continued)

(56) References Cited

U.S. PATENT DOCUMENTS

2006/0191546 A1* 8/2006 Takano .................. A24F 47/002
131/270
2008/0092912 A1 4/2008 Robinson et al.
(Continued)

FOREIGN PATENT DOCUMENTS

JP 2010-506594 A 3/2010
JP 2014-528718 A 10/2014
(Continued)

OTHER PUBLICATIONS

Japanese Office Action and English translation dated Feb. 27, 2018 for Application No. 2016-571660.
(Continued)

*Primary Examiner* — Samchuan C Yao
*Assistant Examiner* — Margaret M Luarca
(74) *Attorney, Agent, or Firm* — Birch, Stewart, Kolasch & Birch, LLP

(57) ABSTRACT

A type flavor inhaler (100) comprises aerosol flow passage (140) guiding aerosol generated by the atomization unit (111) to the mouthpiece side. The aerosol flow passage (140) includes: a first flow passage (140A) which guides aerosol to the mouthpiece side through the flavor source (132); and a second flow passage (140B) which is different from the first flow passage (140A). An aerosol reduction rate of the second flow passage (140B) is smaller than an aerosol reduction rate of the first flow passage (140A).

20 Claims, 9 Drawing Sheets

(51) Int. Cl.
*H05B 1/02* (2006.01)
*A61M 11/04* (2006.01)

(52) U.S. Cl.
CPC ......... *H05B 1/0244* (2013.01); *H05B 1/0297* (2013.01); *A61M 11/045* (2014.02); *H05B 1/0291* (2013.01); *H05B 2203/021* (2013.01)

(58) Field of Classification Search
CPC ........... A24F 40/30; A24F 40/32; A24D 3/04; A24D 3/43; A24D 1/002; A61M 11/02; A61M 11/002; A61M 11/042; A61M 15/06; A61M 15/002
See application file for complete search history.

(56) References Cited

U.S. PATENT DOCUMENTS

2011/0297166 A1* 12/2011 Takeuchi ............. A24F 47/002
131/274

2014/0060556 A1 3/2014 Liu
2015/0335062 A1 11/2015 Shinkawa et al.

FOREIGN PATENT DOCUMENTS

| WO | WO-2013127810 A1 * | 9/2013 | ............. A24D 3/041 |
| WO | WO 2013/159245 A1 | 10/2013 | |
| WO | WO 2014/104078 A1 | 7/2014 | |
| WO | WO 2014/110119 A1 | 7/2014 | |
| WO | WO 2014/115324 A1 | 7/2014 | |

OTHER PUBLICATIONS

International Search Report, issued in PCT/JP2015/066258, PCT/ISA/210, dated Aug. 18, 2015.
Australian Examination Report No. 1, dated May 25, 2018, for Australian Application No. 2015379291.
Korean Office Action, dated Jul. 20, 2018, for Korean Application No. 10-2017-7019002, with an English translation.

* cited by examiner

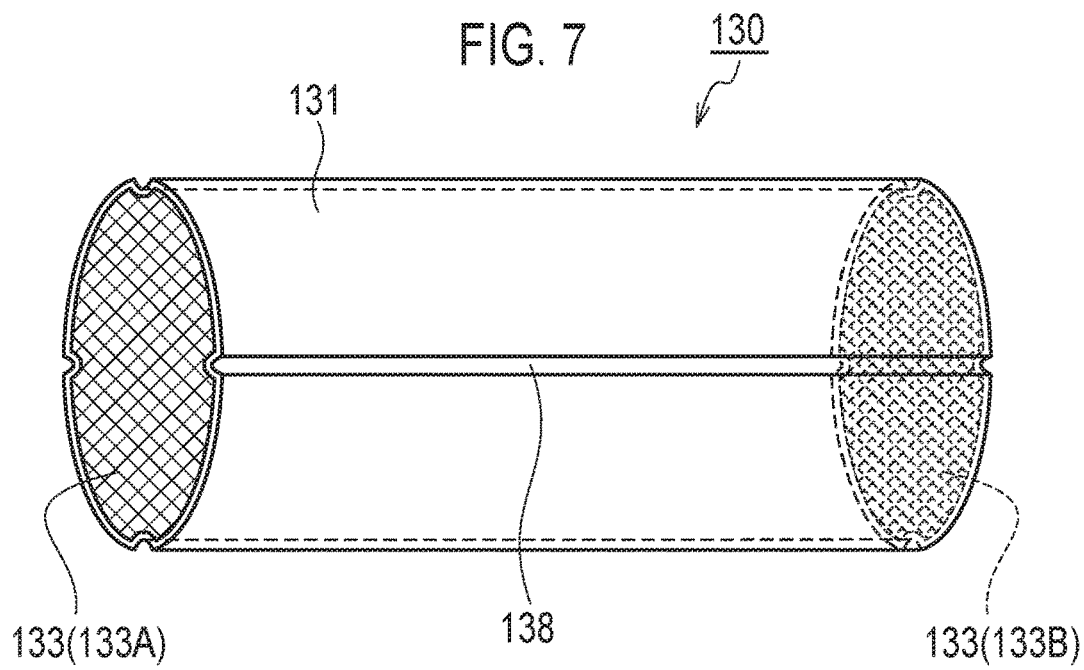
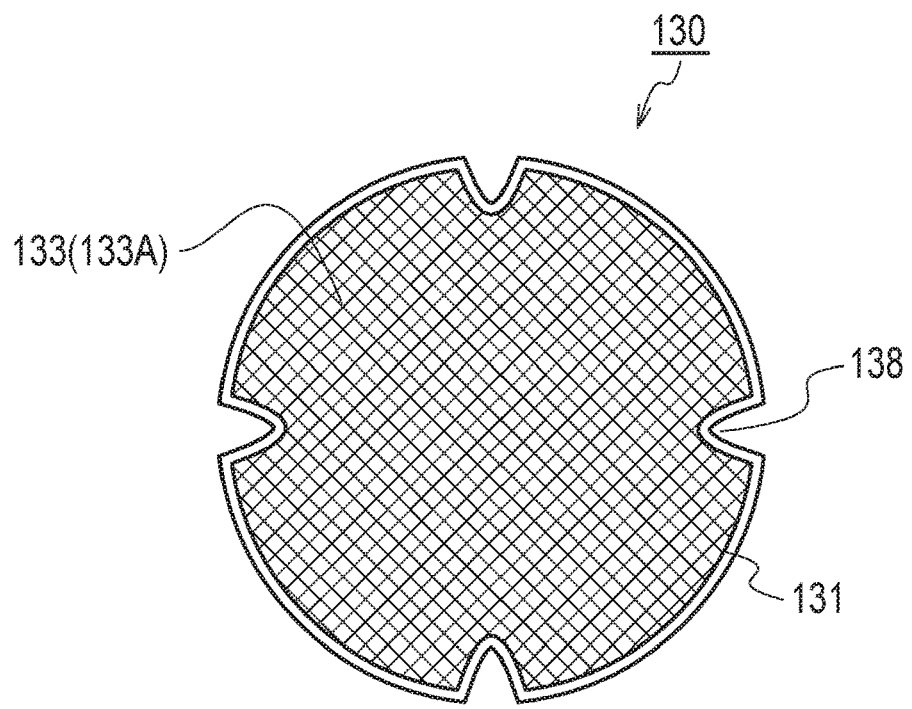

ated by an atomization unit to a mouthpiece side is formed, the atomization unit atomizing an aerosol source without combustion, the aerosol flow passage includes: a

NON-COMBUSTION TYPE FLAVOR INHALER, FLAVOR SOURCE UNIT, AND METHOD FOR MANUFACTURING MEMBER USED IN A NON-COMBUSTION TYPE FLAVOR INHALER

TECHNICAL FIELD

The present invention relates to a non-combustion type flavor inhaler which includes an atomization unit atomizing an aerosol source without combustion, a flavor source unit which is connectable to the non-combustion type flavor inhaler, and a method for manufacturing a member used in a non-combustion type flavor inhaler.

BACKGROUND ART

Conventionally, a non-combustion type flavor inhaler for inhaling flavor without combustion is known. The non-combustion type flavor inhaler includes an atomization unit which atomizes an aerosol source without combustion and a flavor source (for example, a tobacco source) which is provided closer to a mouthpiece side in relation to the atomization unit (for example, Patent Literature 1).

CITATION LIST

Patent Literature

Patent Literature 1: JP 2010-506594 A

SUMMARY

A first feature is summarized as a non-combustion type flavor inhaler comprising: an atomization unit atomizing an aerosol source without combustion; a flavor source provided closer to a mouthpiece side in relation to the atomization unit; and aerosol flow passage guiding aerosol generated by the atomization unit to the mouthpiece side, wherein the aerosol flow passage include: a first flow passage which guides aerosol to the mouthpiece side through the flavor source; and a second flow passage which is different from the first flow passage, and an aerosol reduction rate of the second flow passage is smaller than an aerosol reduction rate of the first flow passage.

A second feature is summarized as the non-combustion type flavor inhaler according to the first feature, wherein the second flow passage is a flow passage which guides aerosol to the mouthpiece side without passing through the flavor source.

A third feature is summarized as the non-combustion type flavor inhaler according to the first feature or the second feature, wherein the atomization unit includes: a first atomization unit which generates aerosol to be guided to the first flow passage; and a second atomization unit which generates aerosol to be guided to the second flow passage.

A fourth feature is summarized as the non-combustion type flavor inhaler according to any one of the first feature to the third feature, wherein the second flow passage is substantially hollow.

A fifth feature is summarized as the non-combustion type flavor inhaler according to any one of the first feature to the fourth feature, wherein the flavor source is a tobacco source.

A sixth feature is summarized as the non-combustion type flavor inhaler according to the fifth feature, wherein the tobacco source has an alkaline pH.

A seventh feature is summarized as the non-combustion type flavor inhaler according to any one of the first feature to the sixth feature, wherein an amount of the aerosol which is guided to the mouthpiece side through the second flow passage is equal to or larger than an amount of the aerosol which is guided to the mouthpiece side through the first flow passage.

An eighth feature is summarized as the non-combustion type flavor inhaler according to any one of the first feature to the seventh feature, wherein the flavor source is formed of raw material pieces which give a flavor element to aerosol generated by the atomization unit.

An ninth feature is summarized as a flavor source unit comprising: a flavor source; and a unit body connectable to an inhaler body included in a non-combustion type flavor inhaler, the unit body storing the flavor source, wherein in a state where the unit body is stored in the inhaler body, at least a part of an aerosol flow passage that guide aerosol generated by an atomization unit to a mouthpiece side is formed, the atomization unit atomizing an aerosol source without combustion, the aerosol flow passage includes: a first flow passage which guides an aerosol to the mouthpiece side through the flavor source; and a second flow passage which is different from the first flow passage, and an aerosol reduction rate of the second flow passage is smaller than an aerosol reduction rate of the first flow passage.

A tenth feature is summarized as the flavor source unit according to the ninth feature, wherein the second flow passage formed in the unit body is a flow passage which guides aerosol to the mouthpiece side without passing through the flavor source.

An eleventh feature is summarized as the flavor source unit according to the ninth feature or the tenth feature, wherein the second flow passage formed in the unit body is formed between an outer surface of the unit body and an inner surface of the inhaler body.

A twelfth feature is summarized as the flavor source unit according to the eleventh feature, wherein the outer surface of the unit body is provided with groove which are opened to at least the mouthpiece-side end, and the groove forms a part of the second flow passage formed in the unit body.

A thirteenth feature is summarized as the flavor source unit according to any one of the ninth feature to twelfth feature, wherein a branch portion at which the flow passage is divided into the first flow passage formed in the unit body and the second flow passage formed in the unit body is provided inside the unit body.

A fourteenth feature is summarized as the flavor source unit according to the ninth feature, wherein the first flow passage formed in the unit body and the second flow passage formed in the unit body are provided inside the unit body.

A fifteenth feature is summarized as the flavor source unit according to any one of the ninth feature to fourteenth feature, wherein the first flow passage formed in the unit body and the second flow passage formed in the unit body are independently formed so as not to intersect each other.

A sixteenth feature is summarized as a method for manufacturing a member used in a non-combustion type flavor inhaler, comprising: a step A of manufacturing an aerosol flow passage forming member that forms at least a part of aerosol flow passage, the aerosol flow passage guiding aerosol generated by an atomization unit to a mouthpiece side, wherein the aerosol flow passage include: a first flow passage which guides aerosol to the mouthpiece side through a flavor source; and a second flow passage which is different from the first flow passage, an aerosol reduction rate of the second flow passage is smaller than an aerosol reduction rate of the first flow passage, and the step A includes a step of determining shapes of the first flow passage and the second flow passage so that an airflow resistance generated in the second flow passage when a gas distributed to the second flow passage passes through the second flow passage is equal to an airflow resistance generated in the first flow passage when a gas distributed to the first flow passage passes through the first flow passage.

A seventeenth feature is summarized as the method according to the sixteenth feature, wherein the step A includes a step of determining the shape of the second flow passage based on the shape of the first flow passage and a flow rate of a gas flowing into the first flow passage.

An eighteenth feature is summarized as the method according to the seventeenth feature, wherein the step A determines the flow rate of the gas flowing into the first flow passage based on an aerosol amount necessary to take out a desired amount of a flavor element from the flavor source.

A nineteenth feature is summarized as the method according to the eighteenth feature, wherein the step A includes a step of determining the aerosol amount necessary to take out a desired amount of the flavor element from the flavor source based on at least one of a type, a size, and a filling amount of a material of raw material pieces forming the flavor source.

A twentieth feature is summarized as the method according to the seventeenth feature, wherein the step A includes a step of determining a shape of the first flow passage to store all raw material pieces forming the flavor source.

A twenty-first feature is summarized as the method according to any one of the sixteenth feature to the twentieth feature, wherein the aerosol flow passages include: a flavor source unit which includes at least the flavor source; and an inhaler body which stores the flavor source unit, and the step A includes a step of manufacturing the flavor source unit and the inhaler body as the aerosol flow passage forming member.

A twenty-second feature is summarized as the method according to any one of the sixteenth feature to the twentieth feature, wherein at least a part of the aerosol flow passage is formed of a flavor source unit including at least the flavor source, and the step A includes a step of manufacturing the flavor source unit as the aerosol flow passage forming member.

A twenty-third feature is summarized as the method according to any one of the sixteenth feature to the twentieth feature, wherein at least a part of the aerosol flow passage is configured by an inhaler body storing the flavor source unit, and the step A includes a step of manufacturing the inhaler body as the aerosol flow passage forming member.

BRIEF DESCRIPTION OF DRAWINGS

FIG. 7 is a diagram illustrating a cartridge 130 according to a third modified example.

FIG. 8 is a diagram illustrating the cartridge 130 according to the third modified example.

DESCRIPTION OF EMBODIMENTS

Next, an embodiment will be described. Note that, the same or similar portions are denoted with the same or similar reference signs in the descriptions of the drawings below. Note that, the drawings are schematic and a ratio of each size is different from a real one.

Therefore, specific sizes and the like should be judged in consideration of the following descriptions. Needless to say, portions of which relationship and ratios of mutual sizes are different between the mutual drawings, are included.

Overview of Embodiment

In view of the above-described background art, the inventors have carried out a careful examination and found that an atomization unit needs to generate aerosol more than a desired aerosol amount in order to allow a user to inhale a desired aerosol since the aerosol is filtered at a flavor source. In other words, the inventors have found that a part of an aerosol source consumption amount and a part of a necessary atomization energy amount are lost.

A non-combustion type flavor inhaler according to an embodiment includes: an atomization unit atomizing an aerosol source without combustion; a flavor source provided closer to a mouthpiece side in relation to the atomization unit; and an aerosol flow passage guiding aerosol generated by the atomization unit to the mouthpiece side. The aerosol flow passage includes: a first flow passage which guides aerosol to the mouthpiece side through the flavor source; and a second flow passage which is different from the first flow passage. An aerosol reduction rate of the second flow passage is smaller than an aerosol reduction rate of the first flow passage.

In the embodiment, the second flow passage, which is different from the first flow passage that guides the aerosol to the mouthpiece side through the flavor source, is provided. The aerosol reduction rate of the second flow passage is smaller than the aerosol reduction rate of the first flow passage. Accordingly, it is possible to efficiently complement a shortfall of the aerosol with the aerosol passing through the second flow passage while a desired amount of a flavor element is taken out from the flavor source by the aerosol passing through the first flow passage. Thus, it is possible to reduce loss of the aerosol source consumption amount and the necessary atomization energy amount.

First Embodiment (Non-Combustion Type Flavor Inhaler)

Figure 1:
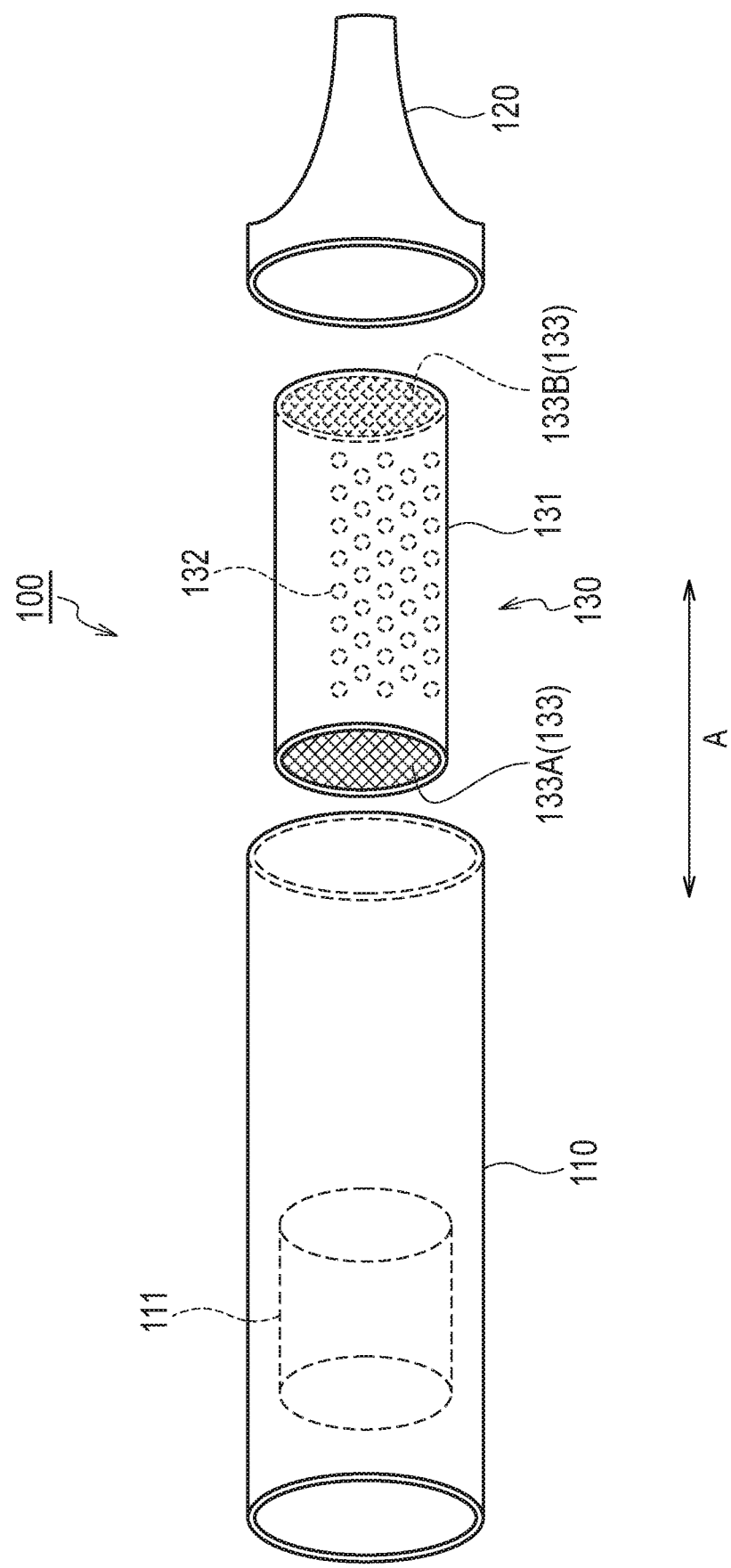
FIG. 1 is a diagram illustrating a non-combustion type flavor inhaler 100 according to a first embodiment.

Hereinafter, a non-combustion type flavor inhaler according to a first embodiment will be described. FIG. 1 is a diagram illustrating a non-combustion type flavor inhaler 100 according to the first embodiment. The non-combustion type flavor inhaler 100 is a mechanism for inhaling a flavor element without combustion and has a shape which extends in a predetermined direction A corresponding to a direction from a non-mouthpiece-side end to a mouthpiece-side end. Additionally, in the description below, it should be noted that the non-combustion type flavor inhaler 100 will be simply referred to as the flavor inhaler 100.

As illustrated in FIG. 1, the flavor inhaler 100 includes an inhaler body 110, a mouthpiece member 120, and a cartridge 130.

The inhaler body 110 is included in a body of the flavor inhaler 100 and has a shape which is connectable to the cartridge 130. The inhaler body 110 includes an atomization unit 111 which atomizes an aerosol source without combustion.

In the first embodiment, the atomization unit 111 includes a reservoir 111P, a wick 111Q, and an atomization portion 111R. The reservoir 111P stores an aerosol source. For example, the reservoir 111P is a porous body which is made of a non-tobacco material such as resin web. The wick 111Q suctions the aerosol source stored in the reservoir 111P. For example, the wick 111Q is made of a glass fiber. The atomization portion 111R atomizes the aerosol source suctioned by the wick 111Q. The atomization portion 111R includes, for example, a heating wire wound around the wick 111Q at a predetermined pitch.

The aerosol source is a liquid such as glycerin or propylene glycol. For example, as described above, the aerosol source is stored in a porous body made of a non-tobacco material such as resin web. Additionally, the aerosol source may include a flavor source containing a nicotine element or the like. Alternatively, the aerosol source may not include the flavor source containing the nicotine element or the like. The aerosol source may include a flavor source containing an element other than the nicotine element. Alternatively, the aerosol source may not include the flavor source containing an element other than the nicotine element.

In the first embodiment, a heating type unit which atomizes the aerosol source by heating is exemplified as the atomization unit 111. However, the atomization unit 111 may be an ultrasonic type unit which atomizes the aerosol source by an ultrasonic wave.

The mouthpiece member 120 includes a mouthpiece which is held by a user and is attachable to and detachable from the inhaler body 110. The mouthpiece member 120 is attached to the inhaler body 110 by, for example, threading or fitting.

The cartridge 130 is an example of a flavor source unit which is connectable to the inhaler body 110 included in the flavor inhaler 100. The cartridge 130 is provided, in a flow passage for a gas (hereinafter, air) inhaled from a mouthpiece, at a position closer to the mouthpiece side in relation to the atomization unit 111. In other words, the cartridge 130 does not need to be essentially provided closer to the mouthpiece side in relation to the atomization unit 111 in terms of a physical space. The cartridge 130 may be provided at a position closer to the mouthpiece side, in relation to the atomization unit 111, in the aerosol flow passage which guides aerosol generated by the atomization unit 111 to the mouthpiece side. That is, in the first embodiment, it may be considered that the "mouthpiece side" is the same as the "downstream" of the flow of the aerosol and the "non-mouthpiece side" is the same as the "upstream" of the flow of the aerosol.

Specifically, the cartridge 130 includes a cartridge body 131, a flavor source 132, and meshes 133 (a mesh 133A and a mesh 133B).

The cartridge body 131 has a cylindrical shape which extends in the predetermined direction A. The cartridge body 131 stores the flavor source 132.

The flavor source 132 is provided, in the flow passage of the air inhaled from the mouthpiece, at a position closer to the mouthpiece side in relation to the atomization unit 111. The flavor source 132 gives a flavor element to aerosol generated from the aerosol source. In other words, flavor given to the aerosol by the flavor source 132 is carried to the mouthpiece.

In the first embodiment, the flavor source 132 is formed of raw material pieces which give a flavor element to the aerosol generated by the atomization unit 111. It is desirable that the size of the raw material pieces be equal to or larger than 0.2 mm and equal to or smaller than 1.2 mm. Further, it is desirable that the size of the raw material pieces be equal to or larger than 0.2 mm and equal to or smaller than 0.7 mm. Since a specific surface area increases as the size of the raw material pieces forming the flavor source 132 decreases, the flavor element is easily released from the raw material pieces forming the flavor source 132. Thus, it is possible to suppress an increase in amount of the raw material pieces when giving a desired amount of the flavor element to the aerosol. As each of the raw material pieces forming the flavor source 132, a body which is obtained by forming shred tobacco or a tobacco raw material into a granular shape can be used. Alternatively, the flavor source 132 may be a body which is obtained by forming a tobacco raw material into a sheet shape. Further, the raw material pieces forming the flavor source 132 may be formed of plants other than tobacco (for example, mint, herb, or the like). A fragrance such as menthol may be given to the flavor source 132.

Here, the raw material pieces forming the flavor source 132 are obtained by sieving according to JIS Z 8815, for example, using a stainless sieve according to JIS Z 8801. For example, raw material pieces passing through a stainless sieve having a mesh size of 0.71 mm are obtained by sieving for 20 minutes according to a dry or mechanical shaking method using a stainless sieve having a mesh size of 0.71 mm. Subsequently, raw material pieces passing through a stainless sieve having a mesh size of 0.212 mm are removed by sieving for 20 minutes according to a dry or mechanical shaking method using a stainless sieve having a mesh size of 0.212 mm. That is, the raw material pieces forming the flavor source 132 are raw material pieces which pass through the stainless sieve (a mesh size=0.71 mm) defining the upper limit and do not pass through the stainless sieve (a mesh size=0.212 mm) defining the lower limit. Thus, in the embodiment, the lower limit of the size of the raw material pieces forming the flavor source 132 is defined by the mesh size of the stainless sieve defining the lower limit. Additionally, the upper limit of the size of the raw material piece forming the flavor source 132 is defined by the mesh size of the stainless sieve defining the upper limit.

In the first embodiment, the flavor source 132 is a tobacco source having an alkaline pH. The pH of the tobacco source is desirably larger than 7 and more desirably equal to or larger than 8. Accordingly, it is possible to efficiently take out the flavor element generated from the tobacco source by the aerosol. Accordingly, it is possible to suppress an increase in amount of the tobacco source when giving a desired amount of the flavor element to the aerosol. Meanwhile, the pH of the tobacco source is desirably equal to or smaller than 14 and more desirably equal to or smaller than 10. Accordingly, it is possible to suppress damage (corrosion or the like) to the flavor inhaler 100 (for example, the cartridge 130 or the inhaler body 110).

Additionally, since the flavor element generated from the flavor source 132 is carried by the aerosol, it should be noted that the flavor source 132 itself does not need to be heated.

The mesh 133A is provided to cover the opening of the cartridge body 131 at the non-mouthpiece side with respect to the flavor source 132, and the mesh 133B is provided to cover the opening of the cartridge body 131 at the mouthpiece side with respect to the flavor source 132. The mesh 133A and the mesh 133B have coarseness with which the raw material piece forming the flavor source 132 do not pass through the mesh. The coarseness of the mesh 133A and the mesh 133B is set to have, for example, a mesh size equal to larger than 0.077 mm and equal to or smaller than 0.198 mm.

(Aerosol Flow Passage)

Figure 2:
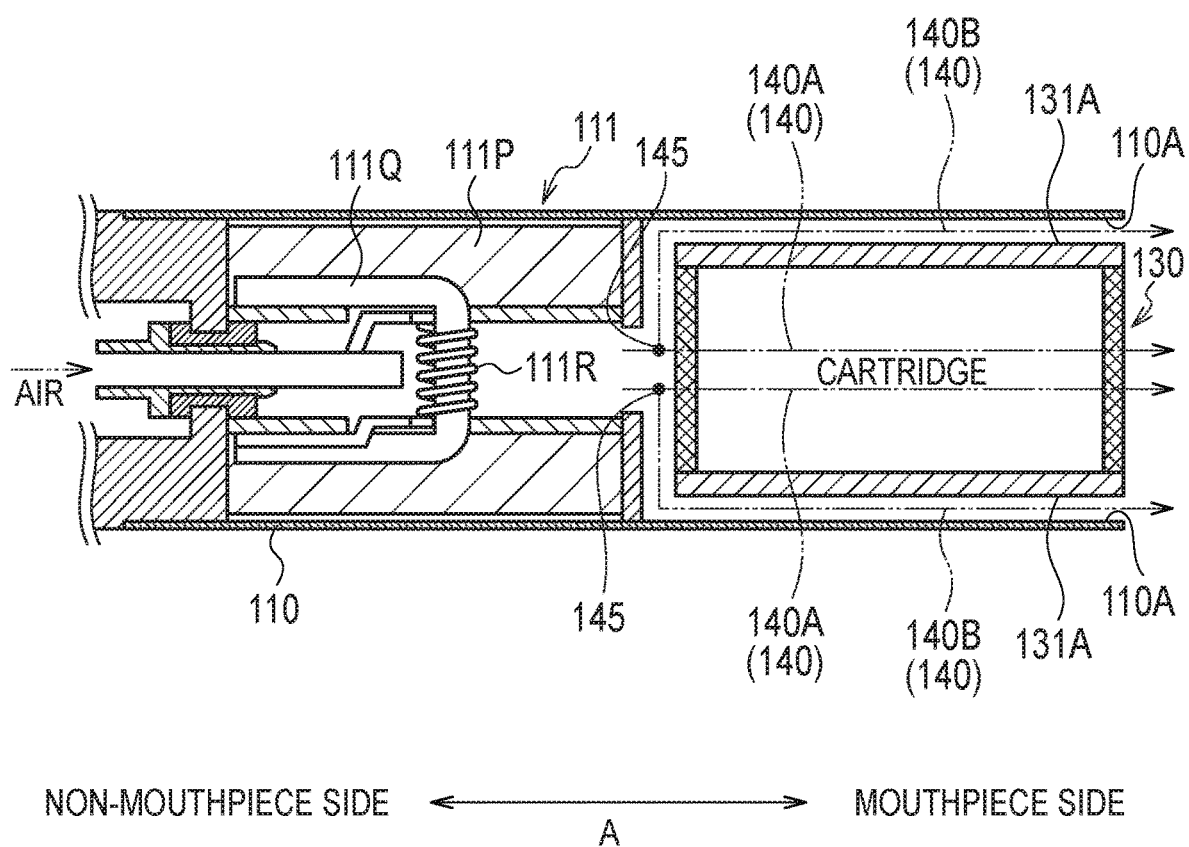
FIG. 2 is a diagram illustrating an aerosol flow passage according to the first embodiment.

Hereinafter, the aerosol flow passage according to the first embodiment will be described. FIG. 2 is a diagram illustrating the aerosol flow passage according to the first embodiment. Specifically, FIG. 2 is a schematic cross-sectional view illustrating an inner structure of the flavor inhaler 100 while the cartridge 130 is stored in the inhaler body 110.

As illustrated in FIG. 2, the flavor inhaler 100 includes aerosol flow passages 140 which guide the aerosol generated by the atomization unit 111 to the mouthpiece side. In other words, the aerosol flow passages 140 which guide the aerosol generated by the atomization unit 111 to the mouthpiece side while the cartridge 130 is stored in the inhaler body 110 is formed. The aerosol flow passages 140 include a first flow passage 140A which guides aerosol to the mouthpiece side through the flavor source 132 and a second flow passage 140B which is different from the first flow passage 140A. The aerosol reduction rate of the second flow passage 140B is smaller than the aerosol reduction rate of the first flow passage 140A. Further, it is desirable that the amount of the aerosol guided to the mouthpiece side through the second flow passage 140B be equal to or larger than the amount of the aerosol guided to the mouthpiece side through the first flow passage 140A. Here, the "reduction rate" indicates a ratio of the "amount of the aerosol lost in the flow passage (the inflow amount−the outflow amount)" with respect to the "amount of the aerosol flowing into the flow passage (the inflow amount)", that is, "(the inflow amount−the outflow amount)/the inflow amount".

In the first embodiment, the second flow passage 140B is a flow passage which guides the aerosol to the mouthpiece side without passing through the flavor source 132. Further, the second flow passage 140B is substantially hollow.

In the first embodiment, the outer diameter of the cartridge body 131 is smaller than the inner diameter of the inhaler body 110 in a cross-section perpendicular to the predetermined direction A. Further, the second flow passage 140B is formed between the outer surface 131A of the cartridge body 131 and the inner surface 110A of the inhaler body 110. Additionally, a branch portion 145 at which a flow passage is divided into the first flow passage 140A and the second flow passage 140E is provided outside the cartridge body 131.

In this way, in the first embodiment, the first flow passage 140A is provided inside the cartridge body 131 and the second flow passage 140B is provided outside the cartridge body 131.

Additionally, the first flow passage 140A and the second flow passage 140B have a common flow passage which is common to each other. The branch portion 145 is provided at the common flow passage between the atomization unit 111 and the cartridge 130. Further, the common portion may be provided at two or more positions. In other words, the first flow passage 140A and the second flow passage 140B may be merged or branched at two or more positions.

In the first embodiment, at least a part of the first flow passage 140A is formed of the inhaler body 110 and the cartridge body 131. At least a part of the second flow passage 140B is formed of the inhaler body 110 and the cartridge body 131.

(Operation and Effect)

In the first embodiment, the second flow passage 140B which is different from the first flow passage 140A guiding the aerosol to the mouthpiece side through the flavor source 132 is provided and the aerosol reduction rate of the second flow passage 140B is smaller than the aerosol reduction rate of the first flow passage 140A. Accordingly, it is possible to efficiently complement the shortfall of the aerosol with the aerosol passing through the second flow passage 140B while a desired amount of the flavor element is taken out from the flavor source 132 by the aerosol passing through the first flow passage 140A. Thus, the loss of the aerosol source consumption amount and the necessary atomization energy amount can be reduced.

In the first embodiment, the second flow passage 140B is a flow passage which guides the aerosol to the mouthpiece side without passing through the flavor source 132. Thus, since the aerosol is not filtered at the flavor source 132 in the second flow passage 140B, a decrease in amount of the aerosol of the second flow passage 140B is suppressed and thus the shortfall of the aerosol can be efficiently complemented. Further, it is possible to suppress a problem in which the flavor source 132 is degraded by the aerosol passing through the second flow passage 140B and to reduce the loss of the aerosol source consumption amount.

In the first embodiment, the second flow passage 140B is substantially hollow. Thus, since a decrease in amount of the aerosol in the second flow passage 140B is further suppressed, the shortfall of the aerosol can be efficiently complemented.

In the first embodiment, the flavor source 132 is a tobacco source having an alkaline pH. Thus, it is possible to efficiently take out the flavor element generated from the tobacco source by the aerosol. Since the flavor element can be efficiently taken out, it is possible to suppress an increase in amount of the tobacco source when obtaining a desired amount of the flavor element.

In the first embodiment, the amount of the aerosol guided to the mouthpiece side through the second flow passage 140B is equal to or larger than the amount of the aerosol guided to the mouthpiece side through the first flow passage 140A. Thus, it is possible to sufficiently guide the aerosol to the mouthpiece side while suppressing degradation of the flavor source 132.

In the first embodiment, the flavor source 132 is formed of the raw material pieces giving the flavor element to the aerosol generated by the atomization unit 111. Accordingly, since a specific surface area increases compared to a body obtained by forming a tobacco raw material into a sheet shape or a sculpted shape, the flavor element can be easily released from the raw material piece forming the flavor source 132. Thus, since it is possible to suppress an increase in volume of the raw material pieces forming the flavor source 132 when giving a desired amount of the flavor element to the aerosol by the flavor source 132, it is possible to suppers an increase in size of the member (here, the cartridge body 131) storing the flavor source 132.

Further, with the raw material pieces having a large specific surface area compared to the body obtained by forming a tobacco raw material into a sheet shape or a sculpted shape, the flavor source 132 is easily degraded. However, since the second flow passage 140B, which is different from the first flow passage 140A guiding the aerosol to the mouthpiece side through the flavor source 132, is provided as described above, degradation of the flavor source 132 is suppressed. That is, since the raw material pieces having a large specific surface area and the second flow passage 140B are employed, it is possible to suppers an increase in size of the member (here, the cartridge body 131) storing the flavor source 132 while suppers degradation of the flavor source 132 and an increase in volume of the raw material pieces forming the flavor source 132.

First Modified Example

Figure 3:
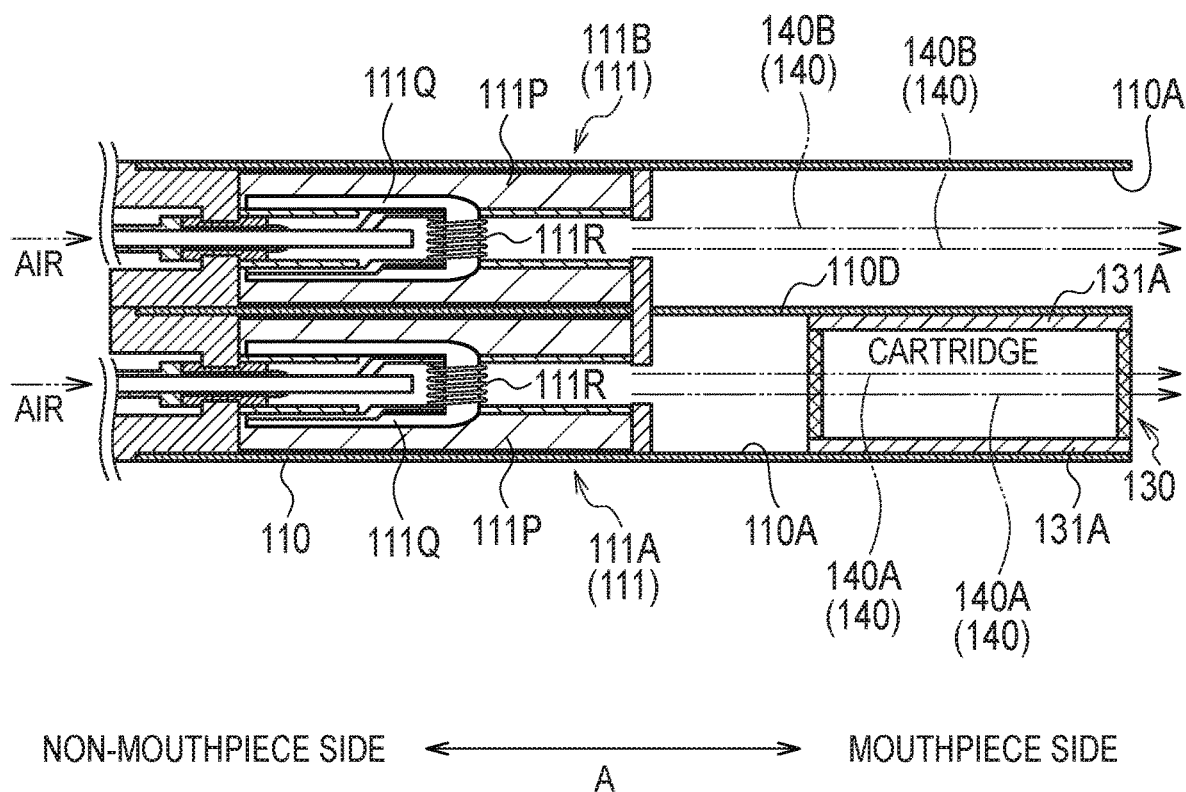
FIG. 3 is a diagram illustrating an aerosol flow passage according to a first modified example.

Hereinafter, a first modified example of the first embodiment will be described with reference to FIG. 3. FIG. 3 is a schematic cross-sectional view illustrating an inner structure of the flavor inhaler 100 while the cartridge 130 is stored in the inhaler body 110. Hereinafter, differences from the first embodiment will be focused in the following description.

Specifically, in the first embodiment, the flavor inhaler 100 includes a single unit which corresponds to the atomization unit 111 for atomizing the aerosol source without combustion. In contrast, in the first modified example, the flavor inhaler 100 includes a first atomization unit 111A which generates the aerosol to be guided to the first flow passage 140A and a second atomization unit 111B which guides the aerosol to be guided to the second flow passage 140B as the atomization unit 111 which atomizes the aerosol source without combustion as illustrated in FIG. 3. Additionally, in the first modified example, since the first flow passage 140A and the second flow passage 140B are divided by a partition portion 110D provided in the inhaler body 110, the branch portion 145 at which a flow passage is divided into the first flow passage 140A and the second flow passage 140B may not be particularly provided.

Additionally, FIG. 3 illustrates only an example of the arrangement of the first flow passage 140A and the second flow passage 140B and an example of the arrangement of the first atomization unit 111A and the second atomization unit 111B. Of course, the arrangement of the first atomization unit 111A and the second atomization unit 111B is not limited to the example illustrated in FIG. 3. Further, the number of the first atomization units 111A and the number of the second atomization units 111B may be set arbitrarily.

In the first modified example, the aerosol source to be atomized by the first atomization unit 111A may be different from the aerosol source to be atomized by the second atomization unit 111B. For example, the aerosol source to be atomized by the first atomization unit 111A may be made of a material which generates the aerosol that easily takes out the flavor element from the flavor source 132. The aerosol source to be atomized by the second atomization unit 111B may be made of a material which generates the aerosol including fragrance. Here, the aerosol source which is atomized by the first atomization unit 111A may be the same as the aerosol source which is atomized by the second atomization unit 111B.

In the first modified example, the first flow passage 140A is mainly formed of the cartridge body 131. The second flow passage 140B is formed of the inhaler body 110.

(Operation and Effect)

In the first modified example, the flavor inhaler 100 includes the first atomization unit 111A which generates the aerosol to be guided to the first flow passage 140A and the second atomization unit 111B which generates the aerosol to be guided to the second flow passage 140B as the atomization unit 111 which atomizes the aerosol source without combustion. Thus, it is possible to improve a degree of freedom in design for the type or the amount of the aerosol for taking out the flavor element from the flavor source 132 and to improve a degree of freedom in design for the type or the amount of the aerosol for complementing the shortfall of the aerosol.

Second Modified Example

Figure 4:
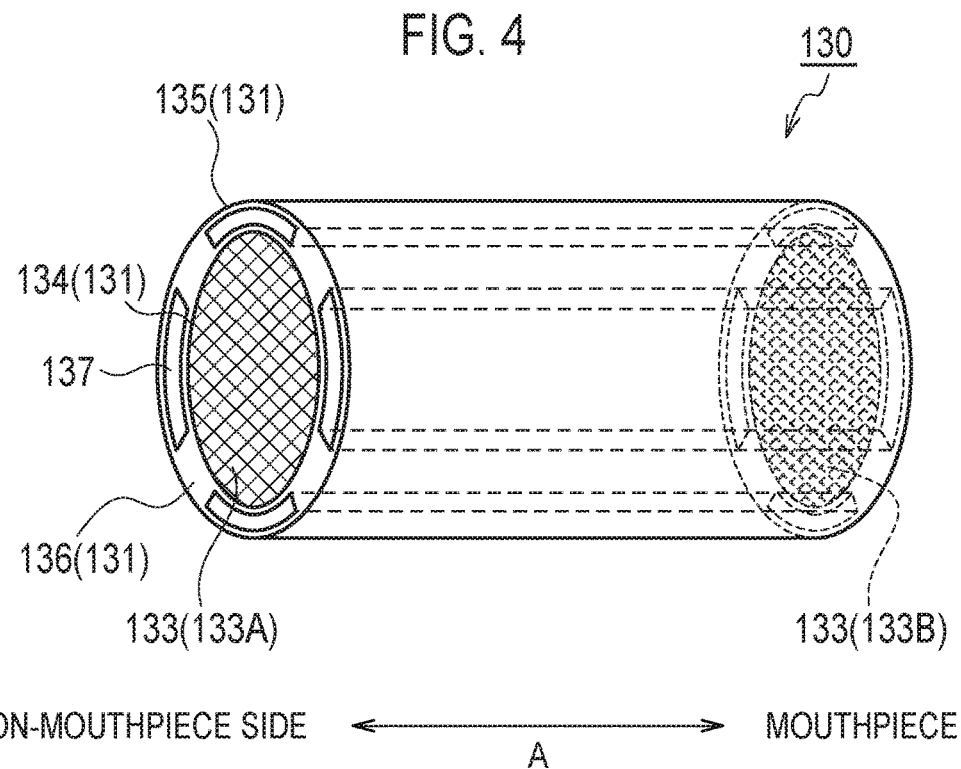
FIG. 4 is a diagram illustrating a cartridge 130 according to a second modified example.
Figure 5:
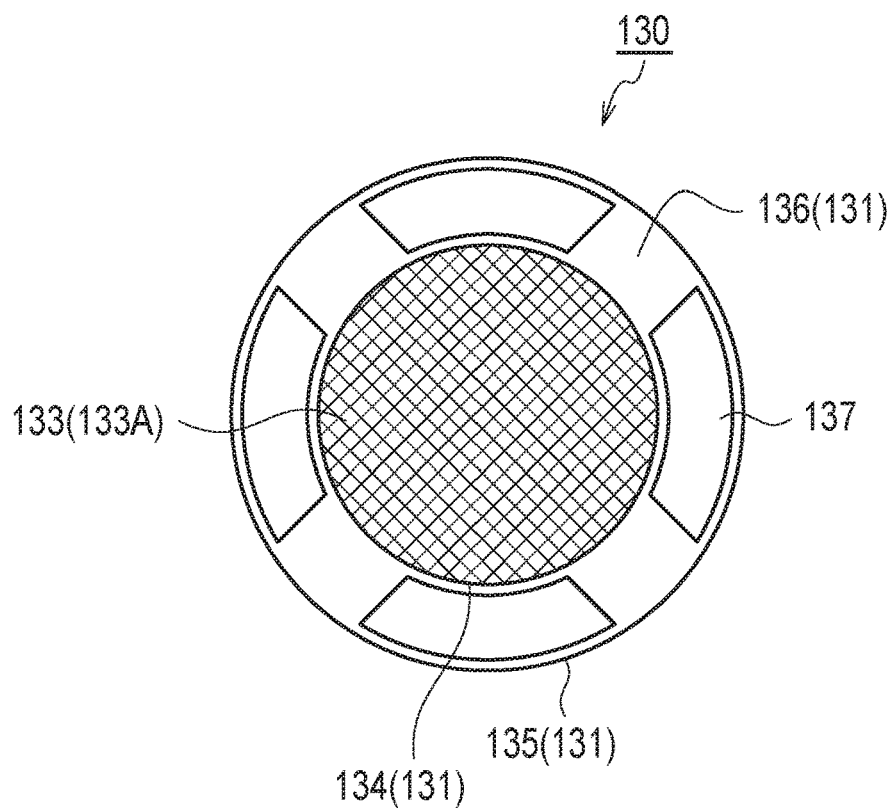
FIG. 5 is a diagram illustrating the cartridge 130 according to the second modified example.
Figure 6:
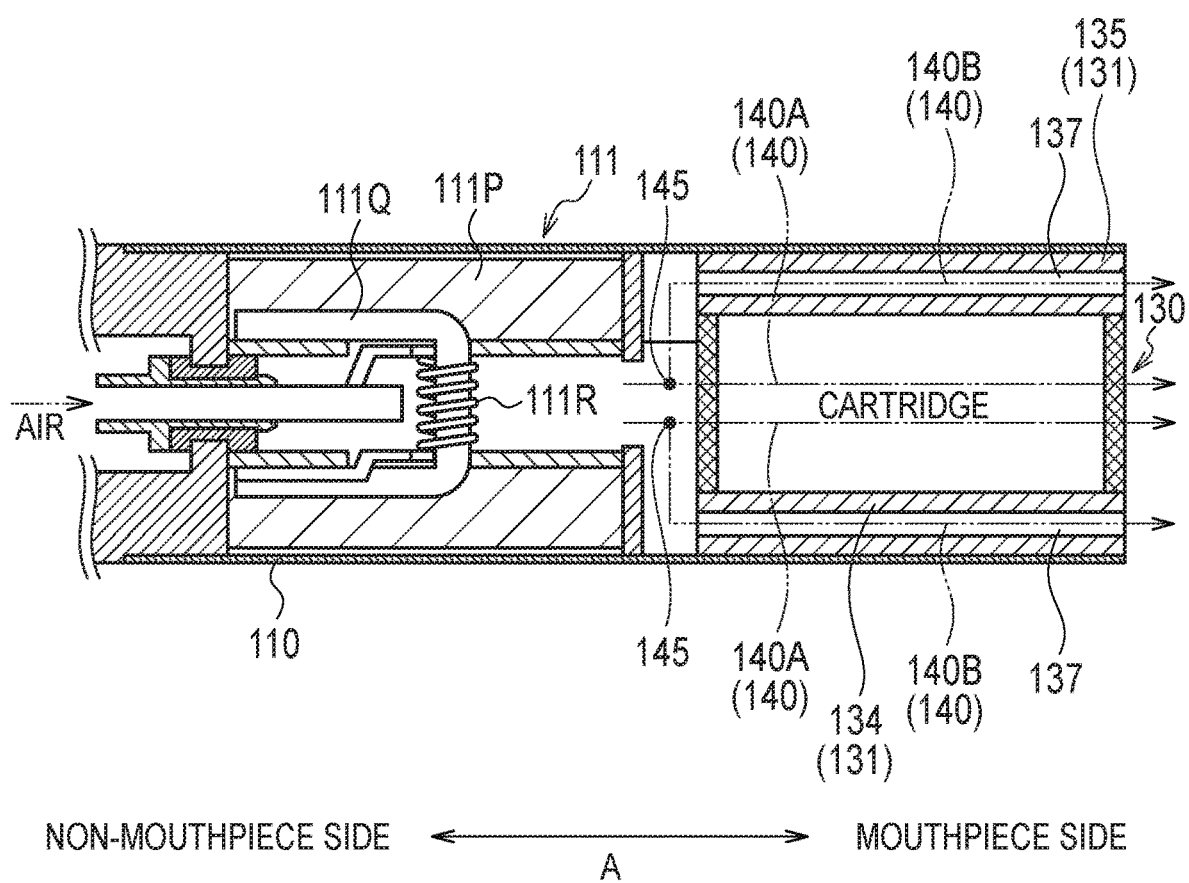
FIG. 6 is a diagram illustrating an aerosol flow passage according to the second modified example.

Hereinafter, a second modified example of the first embodiment will be described with reference to FIGS. 4 to 6. FIG. 4 is a perspective view of the cartridge 130 according to the second modified example and FIG. 5 is a diagram illustrating the cartridge 130 according to the second modified example when viewed from the mouthpiece side. FIG. 6 is a schematic cross-sectional view illustrating an inner structure of the flavor inhaler 100 while the cartridge 130 is stored in the inhaler body 110. Hereinafter, differences from the first embodiment will be focused in the following description.

Specifically, in the first embodiment, the second flow passage 140B is formed between the outer surface 131A of the cartridge body 131 and the inner surface 110A of the inhaler body 110. In contrast, in the second modified example, both the first flow passage 140A and the second flow passage 140B are formed inside the cartridge body 131. In other words, the first flow passage 140A formed in the cartridge body 131 and the second flow passage 140B formed in the cartridge body 131 are formed independently so as not to intersect each other.

Specifically, as illustrated in FIGS. 4 and 5, the cartridge 130 includes the inner body 134, the outer body 135, and the rib 136 as the cartridge body 131. Additionally, it should be noted that the flavor source 132 is omitted in FIG. 4.

The inner body 134 has a cylindrical shape which extends in the predetermined direction A. The inner body 134 stores the flavor source 132. The mesh 133A is provided at the non-mouthpiece side of the inner body 134 and the mesh 133B is provided at the mouthpiece side of the inner body 134.

The outer body 135 has a cylindrical shape which extends in the predetermined direction A. The outer body 135 stores the inner body 134. The outer body 135 is fixed to the inner body 134 by the rib 136 extending in the predetermined direction A.

In the second modified example, the outer body 135 is fixed to the inner body 134 by four ribs 136, and a gap 137 which extends in the predetermined direction A is formed between the adjacent ribs 136.

As illustrated in FIG. 6, in a case using the cartridge 130 according to the second modified example, the first flow passage 140A is a flow passage passing through the inside of the inner body 134 and the second flow passage 140B is a flow passage passing through the gap 137.

In the second modified example, a case in which the cartridge body 131 is formed of the inner body 134, the outer body 135, and the rib 136 has been exemplified. However, the second modified example is not limited thereto. In a mode where both the first flow passage 140A and the second flow passage 140B are formed inside the cartridge body 131, it should be noted that various modifications can be made.

In the second modified example, both the first flow passage 140A and the second flow passage 140B are mainly formed inside the cartridge body 131 and the branch portion 145 at which a flow passage is divided into the first flow passage 140A and the second flow passage 140B is provided outside the cartridge body 131 similarly to the first embodiment.

Additionally, the first flow passage 140A and the second flow passage 140B have a common flow passage which is common to each other. The branch portion 145 is provided at the common flow passage between the atomization unit 111 and the cartridge 130. Further, the common portion may be provided at two or more positions. In other words, the first flow passage 140A and the second flow passage 140B may be merged or branched at two or more positions.

In the second modified example, at least a part of the first flow passage 140A is formed of the inhaler body 110 and the cartridge body 131. At least a part of the second flow passage 140B is formed of the inhaler body 110 and the cartridge body 131.

(Operation and Effect)

In the second modified example, the first flow passage 140A and the second flow passage 140B are formed inside the cartridge body 131. Thus, it is possible to form the second flow passage 140B without changing the design of the inhaler body 110.

Further, it is possible to appropriately form the first flow passage 140A and the second flow passage 140B just by changing the shape of the cartridge 130 in response to the type of the flavor source 132.

Additionally, the inhaler body 110, which is continuously used after replacement of the cartridge 130, is not easily contaminated by the aerosol flow.

Third Modified Example

Figure 9:
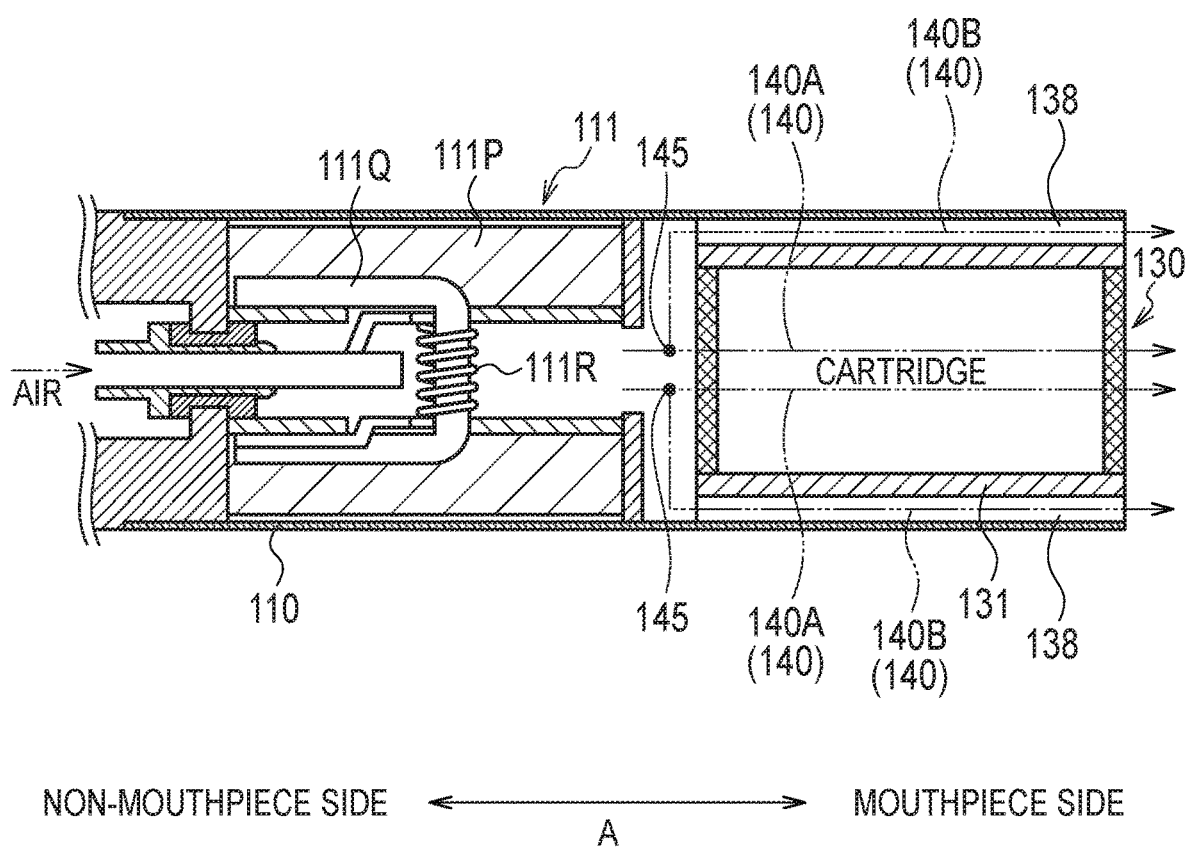
FIG. 9 is a diagram illustrating an aerosol flow passage according to the third modified example.

Hereinafter, a third modified example of the first embodiment will be described with reference to FIGS. 7 to 9. FIG. 7 is a perspective view of the cartridge 130 according to the third modified example and FIG. 8 is a diagram illustrating the cartridge 130 according to the third modified example when viewed from the mouthpiece side. FIG. 9 is a schematic cross-sectional view illustrating an inner structure of the flavor inhaler 100 while the cartridge 130 is stored in the inhaler body 110.

Specifically, in the first embodiment, the outer diameter of the cartridge body 131 is smaller than the inner diameter of the inhaler body 110 in a cross-section perpendicular to the predetermined direction A. In contrast, in the third modified example, the outer surface 131A of the cartridge body 131 other than grooves 138 contacts the inner surface 110A of the inhaler body 110 in a cross-section perpendicular to the predetermined direction A. In such a case, the outer surface 131A of the cartridge body 131 is provided with grooves which extend in the predetermined direction A, from the non-mouthpiece-side end toward the mouthpiece-side end, and is opened to at least the mouthpiece-side end. The groove form a part of the second flow passage 140B.

Specifically, as illustrated in FIGS. 7 and 8, the outer surface 131A of the cartridge body 131 is provided with the grooves 138 which continue from the non-mouthpiece-side end of the cartridge body 131 to the mouthpiece-side end of the cartridge body 131 in the predetermined direction A. In the third modified example, four grooves 138 which extend in the predetermined direction A are exemplified. The groove 138 may be a straight groove or a curved groove.

As illustrated in FIG. 9, in a case using the cartridge 130 according to the third modified example, the first flow passage 140A is a flow passage which passes through the inside of the cartridge body 131 and the second flow passage 140B is a flow passage which passes through the groove 138. That is, the second flow passage 140B is formed of the inner surface 110A of the inhaler body 110 and the groove 138 of the cartridge body 131. In other words, the groove 138 forms a part of the second flow passage 140B.

In the third modified example, a case in which the outer surface 131A of the cartridge body 131 other than the grooves 138 contacts the inner surface 110A of the inhaler body 110 in a cross-section perpendicular to the predetermined direction A has been exemplified. However, the third modified example is not limited thereto. Even in a case where the outer diameter of the cartridge body 131 is smaller than the inner diameter of the inhaler body 110 in a cross-section perpendicular to the predetermined direction A, the outer surface 131A of the cartridge body 131 may be provided with the grooves 138.

In the third modified example, the first flow passage 140A and the second flow passage 140B are divided by the cartridge body 131. Thus, the first flow passage 140A formed in the cartridge body 131 and the second flow passage 140B formed in the cartridge body 131 are independently formed so as not to intersect each other.

Additionally, the first flow passage 140A and the second flow passage 140B have a common flow passage which is common to each other. The branch portion 145 is provided at the common flow passage between the atomization unit 111 and the cartridge 130. Further, the common portion may be provided at two or more positions. In other words, the first flow passage 140A and the second flow passage 140B may be merged or branched at two or more positions.

In the third modified example, at least a part of the first flow passage 140A is formed of the inhaler body 110 and the cartridge body 131. At least a part of the second flow passage 140B is formed of the inhaler body 110 and the cartridge body 131.

(Operation and Effect)

In the third modified example, the outer surface 131A of the cartridge body 131 is provided with the grooves 138 which extend in the predetermined direction A from the non-mouthpiece-side end to the mouthpiece-side end. The groove 138 forms a part of the second flow passage 140B. Thus, it is possible to form the second flow passage 140B without changing the inhaler body 110.

Further, a part of the second flow passage 140B is formed of the inner surface 110A of the inhaler body 110. In other words, a part of the member (the outer body 135) forming the second flow passage 140B is replaced by the inner surface 110A of the inhaler body 110 compared to the second modified example in which all second flow passage 140B is formed of the cartridge 130. Thus, a space for storing the flavor source 132 can be widened outward and a volume for storing, the flavor source 132 increases to a degree corresponding to the thickness of the member (the outer body 135) replaced by the inner surface 110A of the inhaler body 110 compared to the second modified example.

Additionally, since the groove 138 is exposed when the cartridge 130 is separated, the second flow passage 140B can be easily cleaned when the second flow passage 140B formed of the groove 138 is exposed.

Fourth Modified Example

Figure 10:
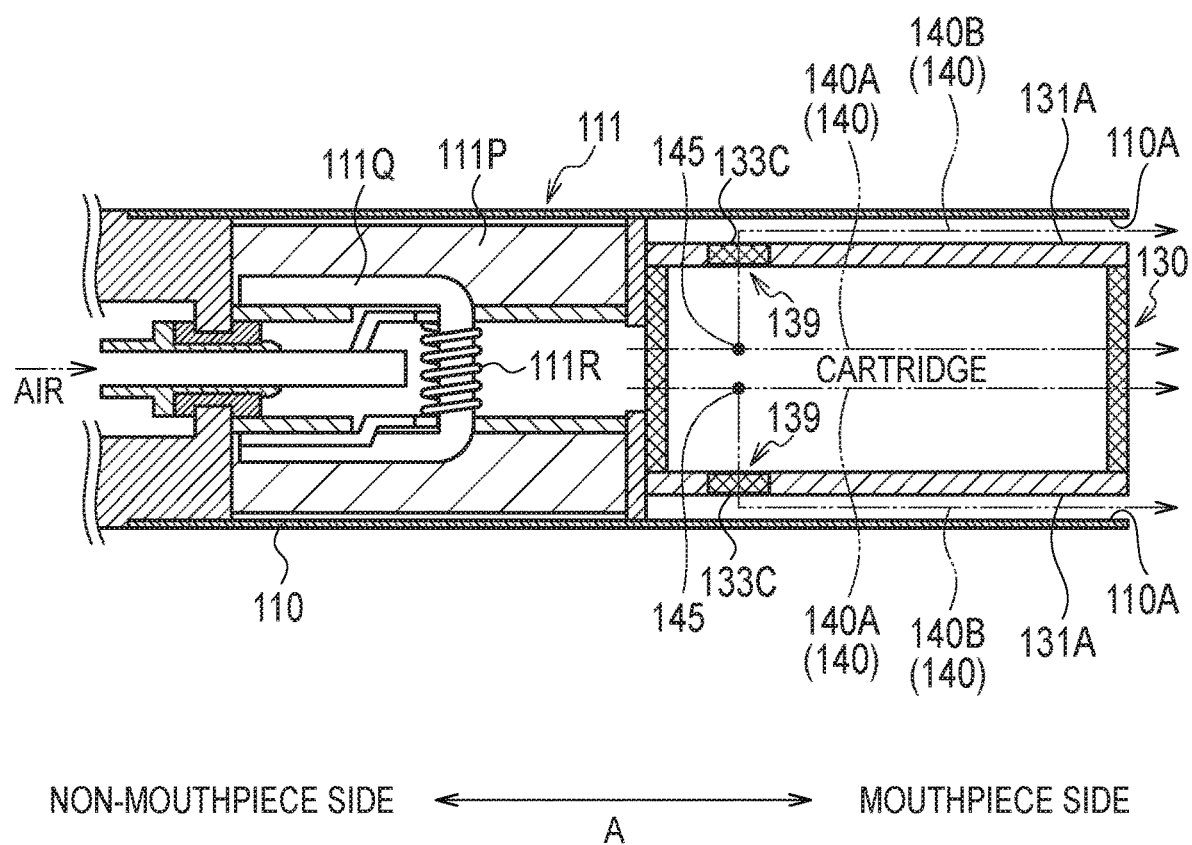
FIG. 10 is a diagram illustrating an aerosol flow passage according to a fourth modified example.

Hereinafter, a fourth modified example of the first embodiment will be described with reference to FIG. 10. FIG. 10 is a schematic cross-sectional view illustrating an inner structure of the flavor inhaler 100 while the cartridge 130 is stored in the inhaler body 110. Hereinafter, a different from the first embodiment will be mainly described.

Specifically, in the first embodiment, the branch portion 145 at which a flow passage is divided into the first flow passage 140A and the second flow passage 140B is provided outside the cartridge body 131. In contrast, in the fourth modified example, the branch portion 145 at which a flow passage is divided into the first flow passage 140A and the second flow passage 140B is provided inside the cartridge body 131 as illustrated in FIG. 10.

In the fourth modified example, the second flow passage 140B which is located at the downstream of the branch portion 145 extends from the inside of the cartridge body 131 to the outside of the cartridge body 131 through an opening hole 139 provided at the side wall of the cartridge body 131. That is, a part of the second flow passage 140B having a hollow shape is formed between the outer surface 131A of the cartridge body 131 and the inner surface 110A of the inhaler body 110. Meanwhile, the aerosol is filtered at the flavor source to be reduced in amount at the first flow passage 140A which is located at the downstream of the branch portion 145. Thus, it should be noted that the aerosol reduction rate of the second flow passage 140B is smaller than the aerosol reduction rate of the first flow passage 140A even when the branch portion 145 is provided inside the cartridge body 131.

In the fourth modified example, the cartridge 130 includes a mesh 133C which is provided to cover the opening hole 139. The mesh 133C has coarseness with which the raw material pieces forming the flavor source 132 do not pass through the mesh. Similar to the mesh 133A and the mesh 133B, the coarseness of the mesh 133C has, for example, a mesh size equal to or larger than 0.077 mm and equal to or smaller than 0.198 mm. Here, the mesh 133C may not be provided when the size of the opening hole 139 is small to a degree in which the raw material pieces forming the flavor source 132 do not pass through.

Here, in the fourth modified example, the non-mouthpiece side end (the upstream end) of the cartridge 130 contacts the mouthpiece side end (the downstream end) of the atomization unit 111. Accordingly, since all aerosol output from the atomization unit 111 is guided to the cartridge 130, the aerosol output from the atomization unit 111 is not guided to the second flow passage 140B without passing through the cartridge 130.

Although it is not specially mentioned in the fourth modified example, both the first flow passage 140A and the second flow passage 140B may be formed inside the cartridge body 131 similarly to the second modified example.

Although it is not specially mentioned in the fourth modified example, the outer surface 131A of the cartridge body 131 may be provided with grooves which extend in the predetermined direction A from the non-mouthpiece-side end to the mouthpiece-side end similarly to the third modified example. The grooves may be continuous from at least the opening hole 139 to the mouthpiece-side end of the cartridge body 131 and may be opened to the mouthpiece-side end. Here, the grooves may be continuous from the non-mouthpiece-side end of the cartridge body 131 to the mouthpiece-side end of the cartridge body 131.

Additionally, the first flow passage 140A and the second flow passage 140B have a common flow passage which is common to each other. The branch portion 145 is provided in the common flow passage formed inside the cartridge body 131. Further, the common portion may be provided at two or more positions. In other words, the first flow passage 140A and the second flow passage 140B may be merged or branched at two or more positions.

In the fourth modified example, at least a part of the first flow passage 140A is formed of the cartridge body 131. At least a part of the second flow passage 140B is formed of the inhaler body 110 and the cartridge body 131.

(Operation and Effect)

In the fourth modified example, the branch portion 145 at which a flow passage is divided into the first flow passage 140A and the second flow passage 140B is provided inside the cartridge body 131. Thus, it is possible to form the second flow passage 140B without changing the design of the inhaler body 110.

Second Embodiment

Figure 11:
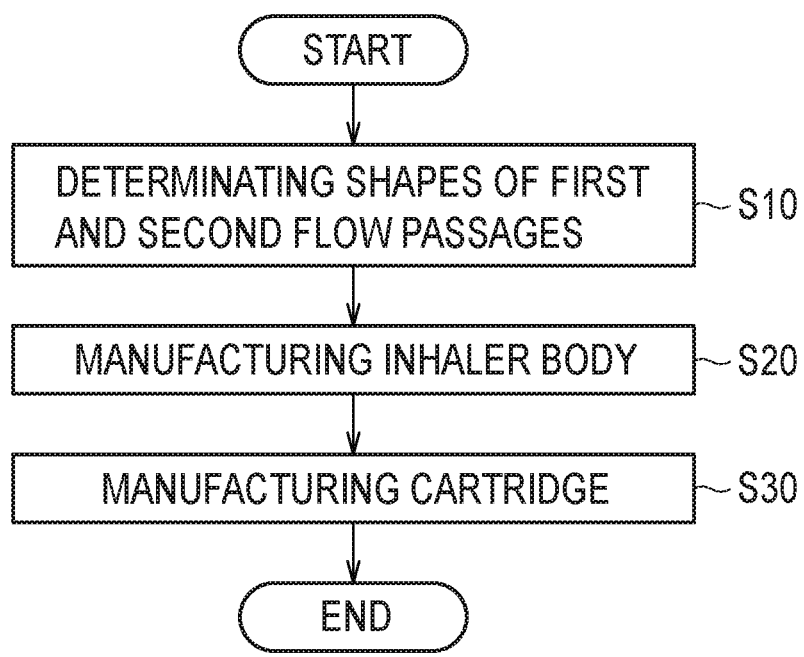
FIG. 11 is a flowchart illustrating a method for manufacturing a non-combustion type flavor inhaler member according to a second embodiment.

Hereinafter, a second embodiment will be described. In the second embodiment, a method for manufacturing a non-combustion type flavor inhaler member will be described with reference to FIG. 11. FIG. 11 is a flowchart illustrating a non-combustion type flavor inhaler member manufacturing method according to the second embodiment. Here, the non-combustion type flavor inhaler member is an aerosol flow passage forming member that forms at least a part of the aerosol flow passages 140 (the first flow passage 140A and the second flow passage 140B).

As illustrated in FIG. 11, in step S10, the shapes of the first flow passage 140A and the second flow passage 140B are determined. Specifically, as will be described later, the shapes of the first flow passage 140A and the second flow passage 140B are determined so that the airflow resistance generated in the second flow passage 140B when air distributed to the second flow passage 140B passes through the second flow passage 140B is the same as the airflow resistance generated in the first flow passage 140A when air distributed to the first flow passage 140A passes through the first flow passage 140A. Further, it is desirable to determine the shape of the second flow passage 140B based on the shape of the first flow passage 140A and the flow rate of the air flowing into the first flow passage 140A. Additionally, it is desirable to determine the flow rate of the air flowing into the first flow passage 140A based on the amount of the aerosol necessary to take out a desired amount of the flavor element from the flavor source 132.

It is desirable to calculate the amount of the aerosol necessary to take out a desired amount of the flavor element based on at least one of the type, the size, and the filling amount of the material of the raw material pieces forming the flavor source 132. Further, it should be noted that the desired amount of the aerosol guided to the mouthpiece side changes based on the amount of the aerosol filtered at the flavor source 132. Additionally, the amount of the aerosol filtered at the flavor source 132 can be also calculated based on parameters including the size and the length of the flow passage of the first flow passage 140A, the length of the charged portion of the flavor source 132 inside the first flow passage 140A, and the type, the size, or the filling amount of the material of the raw material pieces forming the flavor source 132.

In step S20, the inhaler body 110 is manufactured. It should be noted that step S20 is performed based on the shape determination result of the first flow passage 140A and the second flow passage 140B in step S10.

In step S30, the cartridge 130 is manufactured. It should be noted that step S30 is performed based on the shape determination result of the first flow passage 140A and the second flow passage 140B in step 10.

In this way, the non-combustion type flavor inhaler member manufacturing method includes step A of manufacturing the aerosol flow passage forming member forming at least a part of the aerosol flow passage and the step A includes a step of determining the shapes of the first flow passage 140A and the second flow passage 140B so that the airflow resistance generated in the second flow passage 140B when the air distributed to the second flow passage 140B passes through the second flow passage 140B becomes the same as the airflow resistance generated by the first flow passage 140A when the air distributed to the first flow passage 140A passes through the first flow passage 140A.

Here, since a case in which the non-combustion type flavor inhaler member is both the inhaler body 110 and the cartridge 130 has been exemplified, the manufacturing method (step A) includes step S10 to step S30. However, the embodiment is not limited thereto.

For example, when only the inhaler body 110 is manufactured as the non-combustion type flavor inhaler member forming at least a part of the aerosol flow passage 140, the manufacturing method (step A) may include step S10 and step S20. Alternatively, when only the cartridge 130 is manufactured as the non-combustion type flavor inhaler member forming at least a part of the aerosol flow passage 140, the manufacturing method (step A) may include step S10 and step S30.

(Example of Determining Shape of Flow Passage Forming Member)

Hereinafter, an example of step S10 will be described. The first flow passage 140A and the second flow passage 140B are formed of both the inhaler body 110 and the cartridge 130. Here, the first flow passage 140A and the second flow passage 140B may be formed only along the cartridge 130.

(1) Assumption Condition Determination

First, the inhalation flow rate $Q_T$ [mL/min] per each puff operation is determined.

Second, the amount $M_T$ [mg/puff] of the aerosol generated by the atomization unit 111 is determined.

Third, a parameter involving with the flavor source 132 is determined. The parameter is, for example, at least one of the type, the size, and the filling amount of the material of the raw material pieces forming the flavor source 132.

Fourth, the amount $M_1$ of the aerosol necessary to take out a desired amount of the flavor element from the flavor source 132 is determined based on the parameter involving with the flavor source 132.

(2) Determination of Shape of First Flow Passage 140A

The shape of the first flow passage 140A is determined based on the parameter involving with the flavor source 132. Specifically, the shape of the first flow passage 140A is determined based on at least one of the type, the size, and the filling amount of the material of the raw material pieces forming the flavor source 132 so that all members (that is, all raw material pieces forming the flavor source 132) forming the raw material pieces having a predetermined parameter are stored inside the first flow passage 140A.

(3) Derivation of Parameter in First Flow Passage 140A

First, the flow rate $Q_1$ (that is, the flow rate $Q_1$ of the air passing through the flavor source 132) of the air distributed to the first flow passage 140A is obtained based on the above-described assumption condition. Specifically, the air flow rate $Q_1 = Q_T \times V_1$ [mL/min] is calculated by calculating the ratio $V_1 = M_1/M_T$ [%] of the aerosol passing through the flavor source 132.

Second, the airflow resistance $\Delta P_1$ [Pa] generated in the flavor source 132 when the air of the air flow rate $Q_1$ passes through the flavor source 132 is calculated. For example, the airflow resistance values obtained when changing the air flow rate in various ways by an experiment are measured and $\Delta P_1$ at the flow rate $Q_1$ can be estimated based on a regression equation obtained from the obtained plots. Alternatively, the airflow resistance $\Delta P_1$ at the flow rate $Q_1$ may be estimated based on a known theoretical formula or empirical formula for the airflow resistance of the flavor source charged layer.

(4) Determination of Shape of Second Flow Passage 140B

First, the shape of the second flow passage 140B is determined so that the airflow resistance $\Delta P_2$ generated in the second flow passage 140B when the air $(Q_T-Q_1)$ distributed to the second flow passage 140B passes through the second flow passage 140B becomes equal to $\Delta P_1$. For example, when the second flow passage 140B is a single straight cylindrical penetration hole and the flow inside the second flow passage 140B is a laminar flow, the airflow resistance $\Delta P_2$ generated in the second flow passage 140B can be estimated by the following Hagen-Poiseuille's formula.

$$\Delta P_2 = 32 \times \mu \times L \times u/D^2$$

Here, $\mu$ indicates a Kinematic viscosity coefficient [Pa·s] of the air, L: indicates a length [m] of the second flow passage, u indicates the average flow rate [m/s] of the second flow passage, and D indicates the diameter [m] of the second flow passage.

Second, prototyping is performed based on the above-estimated values. Accordingly, it is possible to more accurately determine the shape of the second flow passage 140B.

Here, estimation may be performed using other known fluid simulation methods instead of the Hagen-Poiseuille's formula.

Additionally, it should be noted that prototyping is not an essential process if the accuracy of the various estimated values is high.

In the second embodiment, a case in which the gas distributed to the first flow passage 140A or the second flow passage 140B is air has been exemplified, but the gas distributed to the first flow passage 140A or the second flow passage 140B may be a gas other than air.

(Operation and Effect)

In the second embodiment, the non-combustion type flavor inhaler member manufacturing method includes a step A (in the second embodiment, step S10 to step S30) of manufacturing the aerosol flow passage forming member that forms at least a part of the aerosol flow passages 140 guiding the aerosol generated by the atomization unit 111 to the mouthpiece side. The step A includes a step of determining the shapes of the first flow passage 140A and the second flow passage 140B so that the airflow resistance generated in the first flow passage 140A when the air distributed to the first flow passage 140A passes through the first flow passage 140A becomes the same as the airflow resistance generated in the second flow passage 140B when the air distributed to the second flow passage 140B passes through the second flow passage 140B. Thus, it is possible to appropriately form the first flow passage 140A for taking out a desired amount of the flavor element from the flavor source 132 and the second flow passage 140B for complementing the shortfall of the aerosol. Accordingly, it is possible to suppress a problem in which the flavor source 132 is degraded by the aerosol passing through the second flow passage 140B and to reduce the loss of the aerosol source consumption amount.

In the second embodiment, the step A includes a step of determining the shape of the second flow passage 140B based on the shape of the first flow passage 140A and the flow rate of the air flowing into the first flow passage 140A. Thus, it is possible to easily determine the shape of the second flow passage 140B for complementing the shortfall of the aerosol.

In the second embodiment, the step A determines the flow rate of the air flowing into the first flow passage 140A based on the amount of the aerosol necessary to take out a desired amount of the flavor element from the flavor source. Thus, it is possible to take out a desired amount of the flavor element while complementing the shortfall of the aerosol.

In the second embodiment, the step A includes a step of determining the amount of the aerosol necessary to take out a desired amount of the flavor element from the flavor source based on at least one of the type, the size, and the filling amount of the material of the raw material pieces forming the flavor source. Thus, it is possible to appropriately determine the aerosol amount necessary to take out a desired amount of the flavor element.

In the second embodiment, the step A includes a step of determining the shape of the first flow passage 140A to store all raw material pieces forming the flavor source. Thus, it is possible to appropriately set a shape of the first flow passage 140A for taking out a desired amount of the flavor element.

OTHER EMBODIMENTS

Although the invention has been described by the above-described embodiments, it should not be understood that the discussion and the drawing forming a part of the disclosure limit the invention. From this disclosure, various alternative embodiments, examples, and operational techniques will be apparent to those skilled in the art.

In the embodiment, the cartridge 130 does not include the atomization unit, but the embodiment is not limited thereto. For example, the cartridge 130 may form a single unit along with the atomization unit.

In the embodiment, the flavor source 132 belongs to the cartridge 130 which is connectable to the inhaler body 110 included in the flavor inhaler 100. However, the embodiment is not limited thereto. For example, the inhaler body 110 may store the flavor source 132 without using the cartridge 130.

In the embodiment, a case (the first embodiment, the first modified example, the third modified example) in which the second flow passage 140B is provided inside the cartridge 130, a case (the second modified example) in which the second flow passage 140B is provided outside the cartridge 130, and a case (the fourth modified example) in which the second flow passage 140B is branched inside the cartridge 130 and is provided outside the cartridge 130 have been described. However, the embodiment is not limited thereto. Specifically, the aerosol reduction rate of the second flow passage 140B may be smaller than the aerosol reduction rate of the first flow passage 140A and the number of times in which the second flow passage 140B enters and exits the cartridge 130 toward the downstream of the aerosol flow passage is not limited.

In the embodiment, the outer periphery of the cartridge body 131 and the inner periphery of the inhaler body 110 have a circular shape in a cross-section perpendicular to the predetermined direction A. However, the embodiment is not limited thereto. The outer periphery of the cartridge body 131 and the inner periphery of the inhaler body 110 may have a different shape (for example, a square shape).

INDUSTRIAL APPLICABILITY

According to the embodiments, it is possible to provide a non-combustion type flavor inhaler, a flavor source unit, and a non-combustion type flavor inhaler member manufacturing method capable of reducing the loss of the aerosol source consumption amount and the necessary atomization energy amount.

The invention claimed is:

1. A non-combustion type flavor inhaler comprising:
   an atomization unit configured to atomize an aerosol source without combustion;
   a flavor source provided closer to a mouthpiece side in relation to the atomization unit; and
   an aerosol flow passage configured to guide an aerosol generated by the atomization unit to the mouthpiece side,
   wherein the aerosol flow passage includes:
   a first flow passage configured to guide aerosol to the mouthpiece side through the flavor source; and
   a second flow passage which is different from the first flow passage,
   wherein an aerosol reduction rate of the second flow passage is smaller than an aerosol reduction rate of the first flow passage, and
   wherein the atomization unit includes:
   a first atomization unit configured to generate the aerosol to be guided to the first flow passage; and
   a second atomization unit configured to generate the aerosol to be guided to the second flow passage.

2. The non-combustion type flavor inhaler according to claim 1, wherein the second flow passage is configured to guide aerosol to the mouthpiece side without passing through the flavor source.

3. The non-combustion type flavor inhaler according to claim 1, wherein the second flow passage is substantially hollow.

4. The non-combustion type flavor inhaler according to claim 1, wherein the flavor source is a tobacco source.

5. The non-combustion type flavor inhaler according to claim 4, wherein the tobacco source has an alkaline pH.

6. The non-combustion type flavor inhaler according to claim 1, wherein an amount of the aerosol which is guided to the mouthpiece side through the second flow passage is equal to or larger than an amount of the aerosol which is guided to the mouthpiece side through the first flow passage.

7. The non-combustion type flavor inhaler according to claim 1, wherein the flavor source is formed of raw material pieces which give a flavor element to the aerosol generated by the atomization unit.

8. The non-combustion type flavor inhaler according to claim 1, further comprising a partition provided continuously from the atomization unit to an end of the mouthpiece side.

9. A flavor source unit comprising:
   a flavor source; and
   a unit body connectable to an inhaler body included in a non-combustion type flavor inhaler, the unit body storing the flavor source,
   wherein, in a state where the unit body is stored in the inhaler body, at least a part of an aerosol flow passage that is configured to guide aerosol generated by an atomization unit to a mouthpiece side is formed, the atomization unit configured to atomize an aerosol source without combustion,
   wherein the aerosol flow passage includes:
   a first flow passage configured to guide an aerosol to the mouthpiece side through the flavor source; and
   a second flow passage which is different from the first flow passage, wherein an aerosol reduction rate of the second flow passage is smaller than an aerosol reduction rate of the first flow passage, and wherein the second flow passage is formed in the unit body and is configured to guide the aerosol to the mouthpiece side without passing through the flavor source.

10. The flavor source unit according to claim 9, wherein a branch portion at which the flow passage is divided into the first flow passage formed in the unit body and the second flow passage formed in the unit body is provided inside the unit body.

11. The flavor source unit according to claim 9, wherein the first flow passage formed in the unit body and the second flow passage formed in the unit body are provided inside the unit body.

12. The flavor source unit according to claim 9, wherein the first flow passage formed in the unit body and the second flow passage formed in the unit body are independently formed so as not to intersect each other.

13. A method for manufacturing a member used in a non-combustion type flavor inhaler, comprising:
a step A of manufacturing an aerosol flow passage forming member that forms at least a part of aerosol flow passage, the aerosol flow passage guiding aerosol generated by an atomization unit to a mouthpiece side,
wherein the aerosol flow passage includes:
a first flow passage which guides aerosol to the mouthpiece side through a flavor source; and
a second flow passage which is different from the first flow passage,
wherein the second flow passage is formed in the unit body and guides aerosol to the mouthpiece side without passing through the flavor source,
wherein an aerosol reduction rate of the second flow passage is smaller than an aerosol reduction rate of the first flow passage, and
wherein the step A includes a step of determining shapes of the first flow passage and the second flow passage so that an airflow resistance generated in the second flow passage when a gas distributed to the second flow passage passes through the second flow passage is equal to an airflow resistance generated in the first flow passage when a gas distributed to the first flow passage passes through the first flow passage.

14. The method for manufacturing a member used in a non-combustion type flavor inhaler according to claim 13, wherein the step A includes a step of determining the shape of the second flow passage based on the shape of the first flow passage and a flow rate of a gas flowing into the first flow passage.

15. The method for manufacturing a member used in a non-combustion type flavor inhaler according to claim 14, wherein the step A determines the flow rate of the gas flowing into the first flow passage based on an aerosol amount necessary to take out a desired amount of a flavor element from the flavor source.

16. The method for manufacturing a member used in a non-combustion type flavor inhaler according to claim 15, wherein the step A includes a step of determining the aerosol amount necessary to take out a desired amount of the flavor element from the flavor source based on at least one of a type, a size, and a filling amount of a material of raw material pieces forming the flavor source.

17. The method for manufacturing a member used in a non-combustion type flavor inhaler according to claim 14, wherein the step A includes a step of determining a shape of the first flow passage to store all raw material pieces forming the flavor source.

18. The method for manufacturing a member used in a non-combustion type flavor inhaler according to claim 13, wherein the aerosol flow passages include:
a flavor source unit which includes at least the flavor source; and
an inhaler body which stores the flavor source unit, and
wherein the step A includes a step of manufacturing the flavor source unit and the inhaler body as the aerosol flow passage forming member.

19. The method for manufacturing a member used in a non-combustion type flavor inhaler according to claim 13, wherein at least a part of the aerosol flow passage is formed of a flavor source unit including at least the flavor source, and
wherein the step A includes a step of manufacturing the flavor source unit as the aerosol flow passage forming member.

20. The method for manufacturing a member used in a non-combustion type flavor inhaler according to claim 13, wherein at least a part of the aerosol flow passage is configured by an inhaler body storing the flavor source unit, and
wherein the step A includes a step of manufacturing the inhaler body as the aerosol flow passage forming member.

* * * * *